United States Patent [19]

Levy

[11] Patent Number: 5,169,318
[45] Date of Patent: Dec. 8, 1992

[54] OPTICAL FIBER FOR USE WITH DENTAL LASER

[75] Inventor: Guy Levy, Tustin, Calif.

[73] Assignee: Endo Technic Corporation, San Clemente, Calif.

[21] Appl. No.: 804,918

[22] Filed: Dec. 11, 1991

Related U.S. Application Data

[63] Continuation of Ser. No. 615,789, Nov. 20, 1990, Pat. No. 5,092,773, which is a continuation-in-part of Ser. No. 299,472, Jan. 19, 1989, Pat. No. 5,020,995, and a continuation of Ser. No. 351,203, May 15, 1989, which is a continuation-in-part of Ser. No. 335,245, Apr. 10, 1989, abandoned.

[30] Foreign Application Priority Data

Dec. 21, 1988 [FR] France .................. 88 17549

[51] Int. Cl.⁵ ............................... A61C 5/04
[52] U.S. Cl. .................... 433/226; 433/229; 433/215

[58] Field of Search .......... 433/215, 216, 224, 226, 433/229, 9, 29; 606/10, 3, 13, 15, 16, 92, 93

[56] References Cited

U.S. PATENT DOCUMENTS

| | | | |
|---|---|---|---|
| 4,666,406 | 5/1987 | Kanoa, III | 433/229 |
| 4,764,118 | 8/1988 | Touati et al. | 433/226 |
| 5,007,837 | 4/1991 | Werly | 433/229 |
| 5,030,093 | 7/1991 | Mitnick | 433/229 |

Primary Examiner—Cary E. O'Connor
Attorney, Agent, or Firm—Spensley Horn Jubas & Lubitz

[57] ABSTRACT

A thermoplastic optical fiber for use in treatments requiring filling of openings, recesses, passages, or crevices in mineralized physiologic tissue, the fiber having at least a portion composed of at least one ingredient which is capable of being placed in a flowable state when heated by application of selected laser radiation, is physiologically compatible with the mineralized physiologic tissue and bonds with the mineralized tissue.

16 Claims, 1 Drawing Sheet

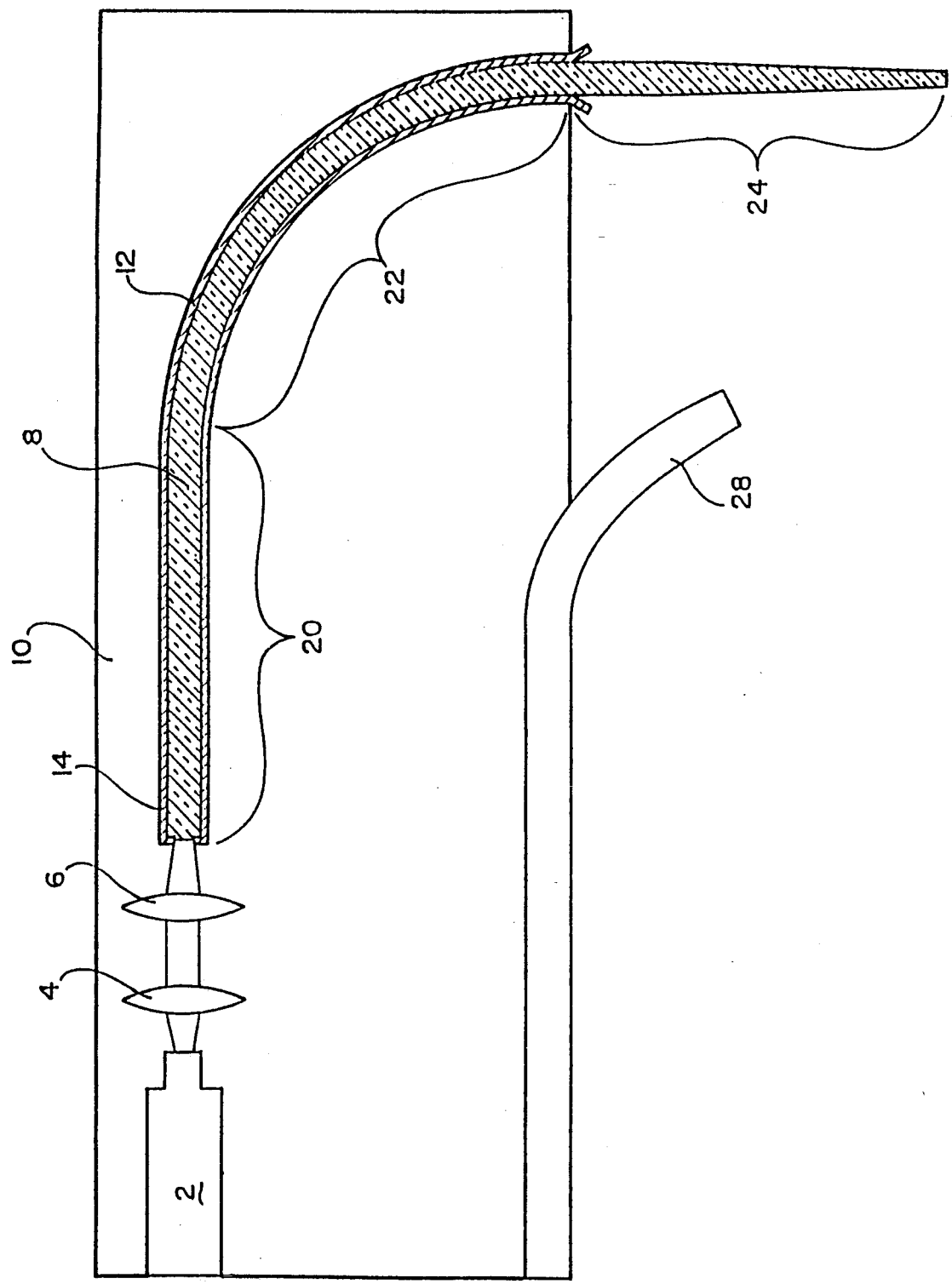

OPTICAL FIBER FOR USE WITH DENTAL LASER

CROSS REFERENCE TO RELATED APPLICATIONS

This is a continuation of application Ser. No. 07/615,789 filed Nov. 20, 1990, now U.S. Pat. No. 5,092,773, which is itself a continuation-in-part of application Ser. No. 07/299,472 filed Jan. 19, 1989, now U.S. Pat. No. 5,020,995, and a continuation of application Ser. No. 07/351,203 filed May 15, 1989, itself a continuation-in-part of application Ser. No. 07/335,245, filed Apr. 10, 1989, now abandoned.

BACKGROUND OF THE INVENTION

The present invention relates to the use of laser radiation for treating mineralized body tissues, including in particular a variety of dental tissues and bone.

The above-cited applications, and in particular application Ser. No. 07/615,789 disclose, inter alia, procedures for filling a tooth or bone cavity by introducing into the cavity the distal end of an optical fiber made of a low melting point composition and then conducting laser radiation having a suitable wavelength and energy level through the fiber in order to melt the fiber, whereby the fiber fills the cavity and bonds to the cavity walls. The result is a filling of a material which is compatible with the tooth tissue, is permanently bonded to the walls of the cavity or opening, and is substantially free of voids.

The prior application also discloses embodiments in which the fiber is provided with a coating selected to enhance various properties of the resulting filling. Examples of coating ingredients included:
- a dark material, such as carbon black, which is highly absorptive of the laser radiation and thus will facilitate melting of the coating in response to a low radiation energy level;
- a ground calcium phosphate material, such a hydroxyapatite, which is a natural component of every mineralized tissue in the body, including bone, enamel, dentin and cementum, and which can serve as a filler which acts to improve biological acceptance, or bodily toleration, of the glass/plastic composition;
- ground ceramic which functions primarily as an inert filler; and/or
- any other composition compatible with the tissue being filled.

SUMMARY OF THE INVENTION

It is an object of the present invention to provide an improved optical fiber for carrying out the abovedescribed filling operations.

Another object of the invention is to provide a dental device which utilizes the improved fiber according to the invention.

Yet another object of the invention is to provide an improved method for filling utilizing improved fibers according to the invention.

The above and other objects according to the invention are achieved by a thermoplastic optical fiber for use in treatments requiring filling of openings, recesses, passages, or crevices in mineralized physiologic tissue, the fiber having at least a portion comprising at least one ingredient which is capable of being placed in a flowable state when heated by application of selected laser radiation, is physiologically compatible with the mineralized physiologic tissue and bonds with the mineralized tissue.

The term "thermoplastic" is employed herein in its literal sense to identify a material which assumes a plastic state upon being heated and solid upon being cooled.

The objects according to the invention are further achieved by a device for filling an opening, recess, passage, or crevice in mineralized physiologic tissue by application of selected laser radiation, the device comprising: a source of such selected laser radiation; and an optical fiber as described above, the optical fiber having a proximal end disposed to receive radiation produced by the source and a distal end arranged to be placed at a location of the mineralized tissue which is to be filled, the portion of the fiber being disposed at the distal end.

The objects according to the invention are further achieved by a method for filling an opening, recess, passage or crevice in mineralized physiological tissue, using the device described above comprising: placing the distal end of the optical fiber in contact with the physiological tissue at a location to be filled; conducting laser radiation from the source and through the optical fiber to the distal end at an energy level and for a duration sufficient to place the at least one ingredient of the optical fiber in the flowable state; and allowing the ingredient which has been placed in the flowable state to solidify.

BRIEF DESCRIPTION OF THE DRAWING

The sole Figure is a side elevational view illustrating the basic components of a device constructed for utilizing the optical fiber according to the present invention.

DESCRIPTION OF THE PREFERRED EMBODIMENTS

The present invention is based essentially on a recognition that a thermoplastic composition capable of forming a high quality filling for a tooth or bone cavity, and particularly a tooth canal, can be given the form of an optical fiber having a diameter small enough to enable the distal end of the fiber to be introduced into the opening, and that the material constituting the fiber can then be melted by conducting suitable laser radiation therethrough. Based on this concept, it is possible to create a composition which is capable of being melted or softened by laser radiation to form a flowable body which conforms precisely to, and bonds intimately with the walls of, the cavity or canal to be filled, and thus forms a filling which is substantially free of voids or gaps, particularly at the interface with the wall of the cavity or canal, and is inert and biologically compatible with the tissue forming the wall of the cavity or canal, or with any other physiological tissue which may come in contact with that body.

Each ingredient of an optical fiber composition according to the invention must satisfy the following requirements:
- it must possess all properties of a material permanently introduced into a physiological system, i.e. it must be compatible with contacting body tissue, chemically stable, durable and non-toxic; and
- it must either be thermoplastic or in finely divided form so as to be encased by a thermoplastic ingredient of the fiber.

In addition, at least one ingredient, which preferably constitutes a major part of the composition, must be thermoplastic, and at least one ingredient must be capable of forming a strong and permanent bond with the tissue constituting the wall of the cavity. Preferably, the thermoplastic ingredient is the same as the ingredient which forms the bond.

Further, the composition or mixture which will be melted by the laser radiation to form the filling must itself be, or must be associated with, a substance capable of absorbing the laser radiation in order to produce the heat needed to achieve the desired melting or softening. This function can be performed by materials which have a dark, or black, coloration with respect to visible light, typical examples being carbon black, or various dark dyes employed in dentistry.

The material employed for absorbing laser radiation may either be mixed into the composition which will be formed into the optical fiber, or may be applied as a coating to the walls of the cavity which is to be filled.

The radiation absorbing substance should be present in a sufficient proportion to absorb at least a substantial portion of the laser radiation which reaches the distal end of the fiber. The greater the amount of radiation absorbed by the selected absorbing material, the lower can be the energy output of the laser.

If the laser energy absorbing material is mixed into the optical fiber, the need for a separate step to apply absorbing material to the cavity walls is eliminated.

As regards the material which is to be melted or softened in order to form the filling, or the basic component of the filling, suitable materials include calcium-containing materials such as apatite, hydroxyapatite, fluorapatite, calcium triphosphate, or dibasic calcium phosphate. Any other material which is physiologically compatible, durable, and capable of forming a substantially void-free mass which is bonded to the cavity walls may be employed.

The thermoplastic ingredient or ingredients of the fiber may make up substantially the entirety of the filling material, or may constitute a matrix in which will be embedded other ingredients which are medically or physiologically beneficial. However, any ingredient of the fiber should be selected to not interfere with the essential goal of creating a filling which is substantially free of voids, forms a permanent bond with the cavity walls, is biologically inert and compatible with the tissue in which it is disposed, and is highly durable.

Fiber compositions according to the invention may also include any suitable glass and/or plastic materials in mixture with a mineral material, preferably a ground calcium phosphate material, which can serve as a filler and act to improve biological acceptance of the filling material, or a ground ceramic material, etc.

The essential characteristics which the fiber should have are that it is composed of a material which is thermoplastic at temperatures which do not cause unacceptable trauma to the tissue in which the cavity is present and which, upon hardening, will have the requisite mechanical properties outlined earlier herein.

According to the invention, the optical fiber composition as described above can constitute the distal end of a fiber, with the remainder of the fiber being made of a conventional glass material. Of course, the distal end portion should have a length sufficient to supply all of the material needed to completely fill the cavity or opening.

According to preferred embodiments of the invention, at least the distal end portion of the fiber consists substantially entirely of a calcium-containing material in thermoplastic form, or a mixture of that material with a radiation absorbing material. The preferred calcium-containing material is hydroxyapatite, which has been found to be capable of being moldable into the form of an optical fiber which is thermoplastic and sufficiently transparent to at least certain laser radiation wavelengths.

The laser radiation applied to the fiber may be in the form of pulses or may be continuous. If continuous, the power level must be adjusted to prevent excessive heating of the tissue bounding the cavity. The radiation wavelength selected will be one which is absorbed by at least one ingredient, for example the ingredient provided specifically for the purpose of absorbing radiation, or by a coating to be applied to the cavity walls. However, a radiation wavelength which is directly absorbed by one, or each, thermoplastic ingredient may also be selected.

One type of radiation which could be employed is that produced by an Nd-YAG laser. However, other types of lasers may be employed.

The Figure illustrates one exemplary of a device which may be equipped with a fiber according to the present invention. Radiation emitted from an Nd:YAG laser 2 is collimated by a converging lens 4. Then, a suitably constructed lens 6 converges the collimated beam into the entrance end of an optical fiber 8. Fiber 8 passes through handpiece 10 and extends out of handpiece 10 by an amount needed to bring the free end of fiber 8 to the tissue region to be treated.

Since a portion at the distal end of optical fiber 8 will be melted or softened and will remain in the opening or recess, it is desirable that fiber 8 be installed in handpiece 10 in a manner to be easily replaceable. This can be achieved most simply by providing handpiece 10 with a fiber guide channel 12 into which fiber 8 can be inserted, and from which it can be withdrawn, but which will gently grip the fiber while accurately positioning its proximal end in alignment with lens 6. The proximal end of channel 12 may be longitudinally slotted to provide fingers 14 which flex radially inwardly to grip the proximal end of fiber 8. Also as shown in the Figure, the proximal ends of fingers 14 may be bent radially inwardly to act as longitudinal abutments for the proximal end of fiber 8. This arrangement also permits different types of fibers, e.g. fibers according to the invention or fibers for performing cutting operations, to be used in a single handpiece.

Fiber 8 may have an overall length of 5 cm, including a straight proximal portion 20 with a length of 1.5 cm, an arcuate middle portion 22 with a length of 1.5 cm and a distal portion 24 with a length of 2 cm.

Preferably, only the distal part of portion 24 is given the thermoplastic composition described above so that a sufficient part of distal portion 24 will remain after a filling operation to permit manual extraction of fiber 8 from channel 12 and replacement with a new fiber.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A thermoplastic optical fiber for use in treatments requiring filling of openings, recesses, passages, or crevices in mineralized physiologic tissue, said fiber having at least a portion which consists of a composition comprising at least one ingredient which is capable of being placed in a flowable state when heated by application of selected laser radiation, is physiologically compatible with the mineralized physiologic tissue and bonds with the mineralized tissue.

2. A fiber as defined in claim 1 wherein said at least one ingredient is a calcium-containing substance.

3. A fiber as defined in claim 1 wherein said calcium-containing substance is at least one of hydroxyapatite, apatite, fluorapatite, calcium triphosphate and dibasic calcium phosphate.

4. A fiber as defined in claim 3 wherein said composition further comprises a second ingredient which is capable of absorbing energy contained in the selected laser radiation.

5. A fiber as defined in claim 4 wherein said second ingredient is present in a finely divided form.

6. A fiber as defined in claim 1 wherein said composition further comprises a calcium-containing substance.

7. A fiber as defined in claim 6 wherein said calcium-containing substance is at least one of hydroxyapatite, apatite, fluorapatite, calcium triphosphate and dibasic calcium phosphate.

8. A fiber as defined in claim 1 wherein said composition further comprises a second ingredient which is capable of absorbing energy contained in the selected laser radiation.

9. A fiber as defined in claim 8 wherein said second ingredient is present in a finely divided form.

10. A fiber as defined in claim 1 wherein said composition consists substantially entirely of a calcium-containing substance.

11. A fiber as defined in claim 10 wherein said composition consists substantially entirely of hydroxyapatite.

12. A device for filling an opening, recess, passage, or crevice in mineralized physiologic tissue by application of selected laser radiation, said device comprising: a source of such selected laser radiation; and an optical fiber as defined in claim 1, said optical fiber having a proximal end disposed to receive radiation produced by said source and a distal end arranged to be placed at a location of the mineralized tissue which is to be filled, said portion of said fiber being disposed at said distal end.

13. A device as defined in claim 12 wherein said at least one ingredient is a calcium-containing substance.

14. A device as defined in claim 12 wherein said composition further comprises a second ingredient which is capable of absorbing energy contained in the selected laser radiation.

15. A device as defined in claim 12 wherein said composition further comprises a calcium-containing substance.

16. A method for filling an opening, recess, passage or crevice in mineralized physiological tissue, using the device defined in claim 12, comprising: placing the distal end of the optical fiber in contact with the physiological tissue at a location to be filled; conducting laser radiation from the source and through the optical fiber to the distal end at an energy level and for a duration sufficient to place the at least one ingredient of the optical fiber in the flowable state; and allowing the ingredient which has been placed in the flowable state to solidify.

* * * * *